United States Patent
Al Rashed

(10) Patent No.: US 12,421,865 B2
(45) Date of Patent: Sep. 23, 2025

(54) METHOD OF GAS TURBINE LEL SENSOR REMOTE GAS CALIBRATION

(71) Applicant: SAUDI ARABIAN OIL COMPANY, Dhahran (SA)

(72) Inventor: Ibrahim S. Al Rashed, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 14 days.

(21) Appl. No.: 18/326,771

(22) Filed: May 31, 2023

(65) Prior Publication Data

US 2024/0401497 A1 Dec. 5, 2024

(51) Int. Cl.
*G01N 33/00* (2006.01)
*F01D 21/00* (2006.01)
*F01D 25/24* (2006.01)

(52) U.S. Cl.
CPC ........... *F01D 21/003* (2013.01); *F01D 25/24* (2013.01); *G01N 33/00* (2013.01); *G01N 33/0006* (2013.01); *F05D 2260/83* (2013.01)

(58) Field of Classification Search
CPC ....... F01D 21/003; F01D 25/24; G01N 33/00; G01N 33/0006; F05D 2260/83
See application file for complete search history.

(56) References Cited

U.S. PATENT DOCUMENTS

| | | | |
|---|---|---|---|
| 8,220,308 B2 | 7/2012 | Bellis et al. | |
| 2004/0055359 A1* | 3/2004 | Ketler | G01N 33/0006 702/100 |
| 2011/0072879 A1* | 3/2011 | Bellis | G01N 33/0006 73/1.06 |

FOREIGN PATENT DOCUMENTS

CN 107933239 A 4/2018

OTHER PUBLICATIONS

Emerson, "Oil and Gas Industry—Safety Monitoring"; <https://www.emerson.com/documents/automation/application-note-oil-gas-industry-safety-monitoring-rosemount-en-72588.pdf>; Accessed May 31, 2023 (10 pages).
General Monitors, "Automatic Remote Gas Calibrator [ARGC]"; <https://s7d9.scene7.com/is/content/minesafetyappliances/ARGC%20Data%20Sheet>; Accessed May 31, 2023 (2 pages).

* cited by examiner

*Primary Examiner* — Xin Y Zhong
(74) *Attorney, Agent, or Firm* — Osha Bergman Watanabe & Burton LLP

(57) ABSTRACT

A remote gas calibration (RGC) assembly is used for preventive maintenance of a gas sensor installed in an inaccessible location inside of a gas turbine equipment. The RGC assembly includes a connector adapted to couple to the gas sensor, where the connector is connected to a first end of a tubing, a needle valve adapted to control flow of gas through the tubing, where the needle valve is connected to a second end of the tubing, and a smart gas monitor in flow communication with the tubing and adapted to record data related to the flow of gas through the tubing. The tubing has a length that allows the needle valve to be placed in an accessible location external to the gas turbine equipment when the connector is coupled to the gas sensor.

6 Claims, 4 Drawing Sheets

METHOD OF GAS TURBINE LEL SENSOR REMOTE GAS CALIBRATION

BACKGROUND

A gas turbine is combustion engine equipment in a power plant that consumes natural gas, oil, or other liquid fuels to generate mechanical energy. The generated energy may be used to drive a generator to produce electrical energy, e.g., to be supplied to homes and businesses.

LEL stands for "Lower Explosive Limit" and is the lowest concentration of a particular gas or fume that has the potential to be flammable or combustible. In other words, LEL is the minimum amount of gas or fume that will catch fire or explode when an ignition source is present. If a gas/fume concentration is less than the LEL, there is insufficient gas/fume to ignite.

Distributed Control Systems (DCS) are extensively used automation control systems in the oil and gas industry. These systems offer improved control over the production process. The oil and gas industry is a process-based industry that is characterized by continuous operations and complex monitoring processes. DCS automate safety processes, such as alarm management system, and undertake corrective measures and predictive maintenance of equipment.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein to a remote gas calibration (RGC) assembly for preventive maintenance of a gas sensor installed in an inaccessible location inside of a gas turbine equipment. The RGC assembly includes a connector having a gassing nozzle adapted to couple to the gas sensor, wherein the connector is connected to a first end of a tubing. The RGC assembly also includes a needle valve adapted to control flow of gas through the tubing, wherein the needle valve is connected to a second end of the tubing. The tubing may have a length that allows the needle valve to be placed in an accessible location external to the gas turbine equipment when the connector is coupled to the gas sensor inside the gas turbine equipment. The RGC assembly may also include a smart gas monitor in flow communication with the tubing and adapted to record data related to the flow of gas through the tubing.

In general, in another aspect, embodiments of the present disclosure relate to a gas turbine that includes a plurality of compartments for housing respective components of the gas turbine, a gas sensor installed in an inaccessible location inside of at least one of the plurality of compartments, and a remote gas calibration (RGC) assembly. The RGC assembly includes a connector having a gassing nozzle that is coupled to the gas sensor, wherein the connector is connected to a first end of a tubing, and a needle valve adapted to control flow of gas through the tubing, wherein the needle valve is connected to a second end of the tubing. The tubing may have a length that allows the needle valve to be placed in an accessible location external to the gas turbine. The RGC assembly also includes a smart gas monitor in flow communication with the tubing and adapted to record data related to the flow of gas through the tubing.

In general, in yet another aspect, embodiments disclosed herein relate to a method for preventive maintenance of a gas sensor in a gas turbine. The method includes (i) installing a remote gas calibration (RGC) assembly to the gas turbine by coupling a connector of the RGC assembly to the gas sensor, wherein the gas sensor is installed in an inaccessible location inside a gas turbine equipment of the gas turbine, and wherein, when the RGC assembly is installed, the RGC assembly has a tubing that extends from the connector coupled to the gas sensor inside the gas turbine equipment to an accessible location external to the gas turbine equipment, and wherein a needle valve is provided at an external end of the tubing in the accessible location, (ii) directing a gas through the needle valve and the tubing to the gas sensor, (iii) detecting, using a sensing element in a smart gas monitor provided in flow communication with the tubing, the gas present in the tubing, (iv) determining and recording, using a calibration analyzer in the smart gas monitor, data associated with the gas directed through the tubing, and (v) wirelessly transmitting, using the calibration analyzer, the data to a gateway of a distributed control system (DCS) of the gas turbine.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of this disclosure provide a system and a method for performing preventive maintenance remotely for gas turbine equipment. Throughout this disclosure, the term "remote" refers to any accessible location away from a gas sensor installed inside a gas turbine compartment. Specifically, the accessible location is external to the gas turbine compartment and is accessible without entering or otherwise reaching inside the compartment.

In one or more embodiments of the invention, LEL sensors are installed in gas turbine equipment, e.g., at least one of an air intake duct, combustion compartment, turbine compartment, control compartment, accessory compartments, or other gas turbine compartment, in to detect unexpected gas leaks that may happen and cause explosion or undesired incidents. LEL sensors may include a gas sensor (e.g., catalytic or infrared (IR)) that is configured to measure an amount of LEL combustible gas. The LEL sensors are inaccessible and require regular preventive maintenance (e.g., monthly) for gas monitoring calibration to ensure that the LEL sensors' functionality is within specification. In one or more embodiments, a Remote Gas Calibration (RGC) assembly is installed as a retrofit to each of the inaccessible LEL sensor locations for performing preventive maintenance testing and other tasks remotely with no need to access sensors inside gas turbine compartments. Embodiments provide easy access to calibrate the LEL sensors, minimize maintenance equipment hours, increase work mobility, achieve fast maintenance completion time, ensure personal safety, achieve optimum equipment's operation reliability, and minimize usage of scaffolding and associated potential hazards.

Figure 1:
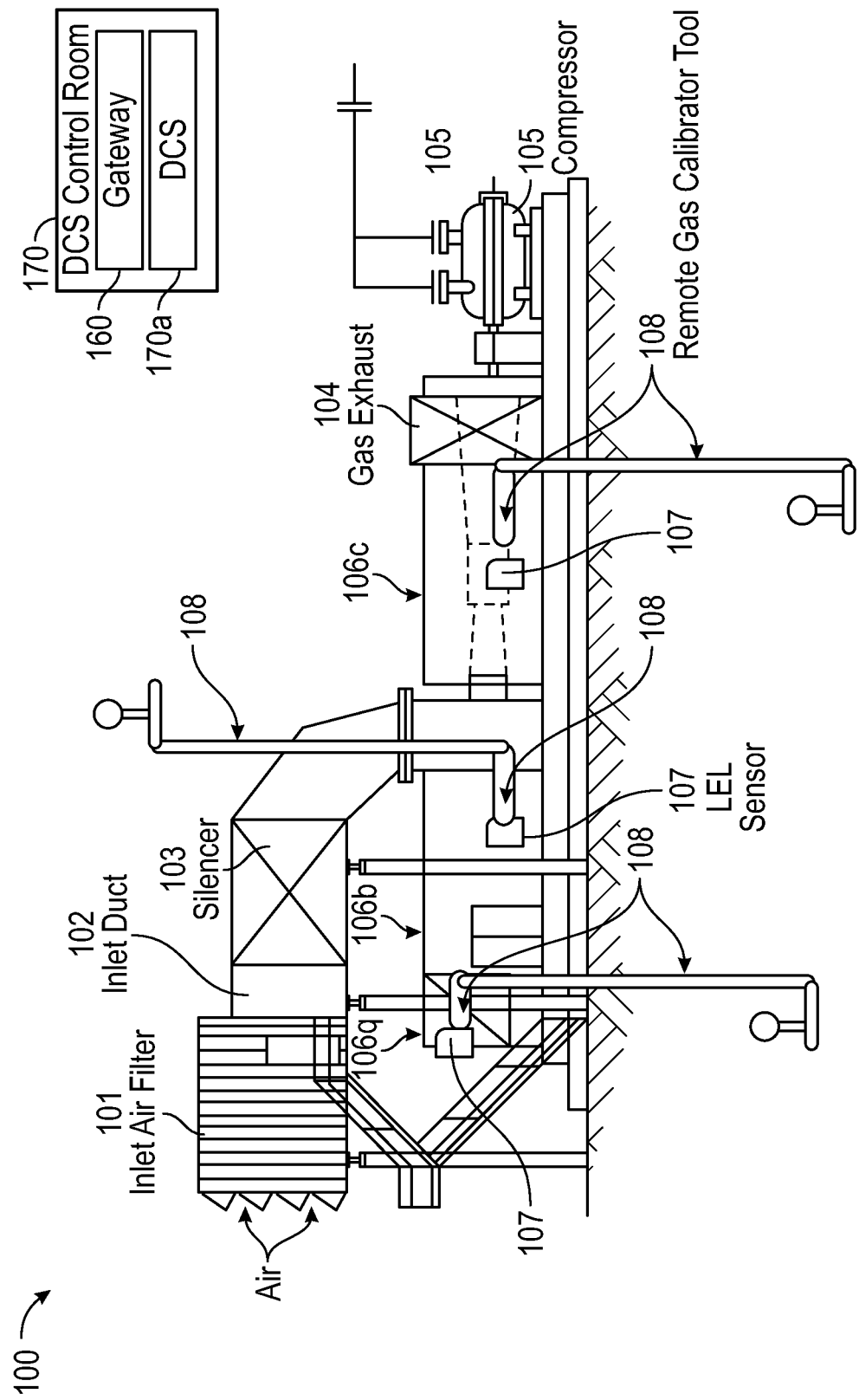
FIGS. 1 and 2 show a system in accordance with one or more embodiments.

FIG. 1 shows a schematic diagram in accordance with one or more embodiments. As shown in FIG. 1, a gas turbine (100) includes an inlet air filter (101), an inlet duct (102), a silencer (103), a gas exhaust (104), a compressor (105), and multiple compartments (106a, 106b, 106c). For example, the compartments of the gas turbine (100) include a control compartment (106a), an accessory compartment (106b), and a turbine compartment (106c) where each compartment has an initially installed an LEL sensor (107) and is subsequently retrofitted with an RGC assembly (108). In one or more embodiments, each LEL sensor (107) and retrofitted RGC assembly (108) are communicably coupled to a gateway (160) of a DCS (170a) in a DCS control room (170). The DCS control room (170) may be located in the gas turbine facility where the gas turbine (100) is installed.

In an example installation, the gas turbine facility is an oil and gas facility that requires reliable best practices and adaptive solutions to reach the maximum equipment benefits for better operation and maintenance performances. A major part of the operation and maintenance tasks is based on preventive maintenance procedures for turbine compartments, sensors calibration, ducts cleaning, and filters replacement. Flammable gas leaks out of fuel gas supply system or generator of the gas turbine (100) may expose one or more of the compartments (106a, 106b, 106c) to risk of explosion or fire. Installed LEL sensors (107) in the compartments (106a, 106b, 106c) are configured to detect abnormal levels of explosive gases. Over time the LEL sensors (107) may deteriorate and become inefficient due to fouling and exposure to extensive high temperatures, which may cause an increase of false alarms or unexpected sensor failures. Traditional sensor maintenance and calibration cycles can be very difficult to implement due to location inaccessibility with confined spaces and constraints inside gas turbine compartments. In addition, entering the gas turbine compartments requires production shutdown and extended down time for cooling of turbine as well as erecting scaffolding in order to access the LEL sensors leading to further increase of turbine operation outages.

In one or more embodiments, the deficiencies of the traditional sensor maintenance and calibration cycles are eliminated or otherwise improved by installing the RGC assemblies (108) to retrofit all inaccessible LEL sensors (107) to allow performing sensor calibration and testing remotely without entering into the compartments or shut down the gas turbine (100). In some embodiments, LEL sensors (107) may be initially installed with RGC assemblies (108) to allow remote sensor calibration and testing. The remote sensor calibration and testing saves work load time, man power and mitigates potential risk encountered while conducting preventive maintenance for all inaccessible sensors.

In some embodiments, the gateway (160) may include hardware and/or software that serve as a communication interface to allow a user to initiate and monitor remote LEL sensor calibration and testing via the existing DCS (170a). While the gateway (160) is shown on top (e.g., ceiling or roof) of the DCS control room (170), in alternative embodiments the gateway (160) may also be located inside the DCS control room (170). Further, the DCS (170a) (160) may include a computer system that is similar to the computer system (400) described below with regard to FIG. 4 and the accompanying description.

Figure 2:
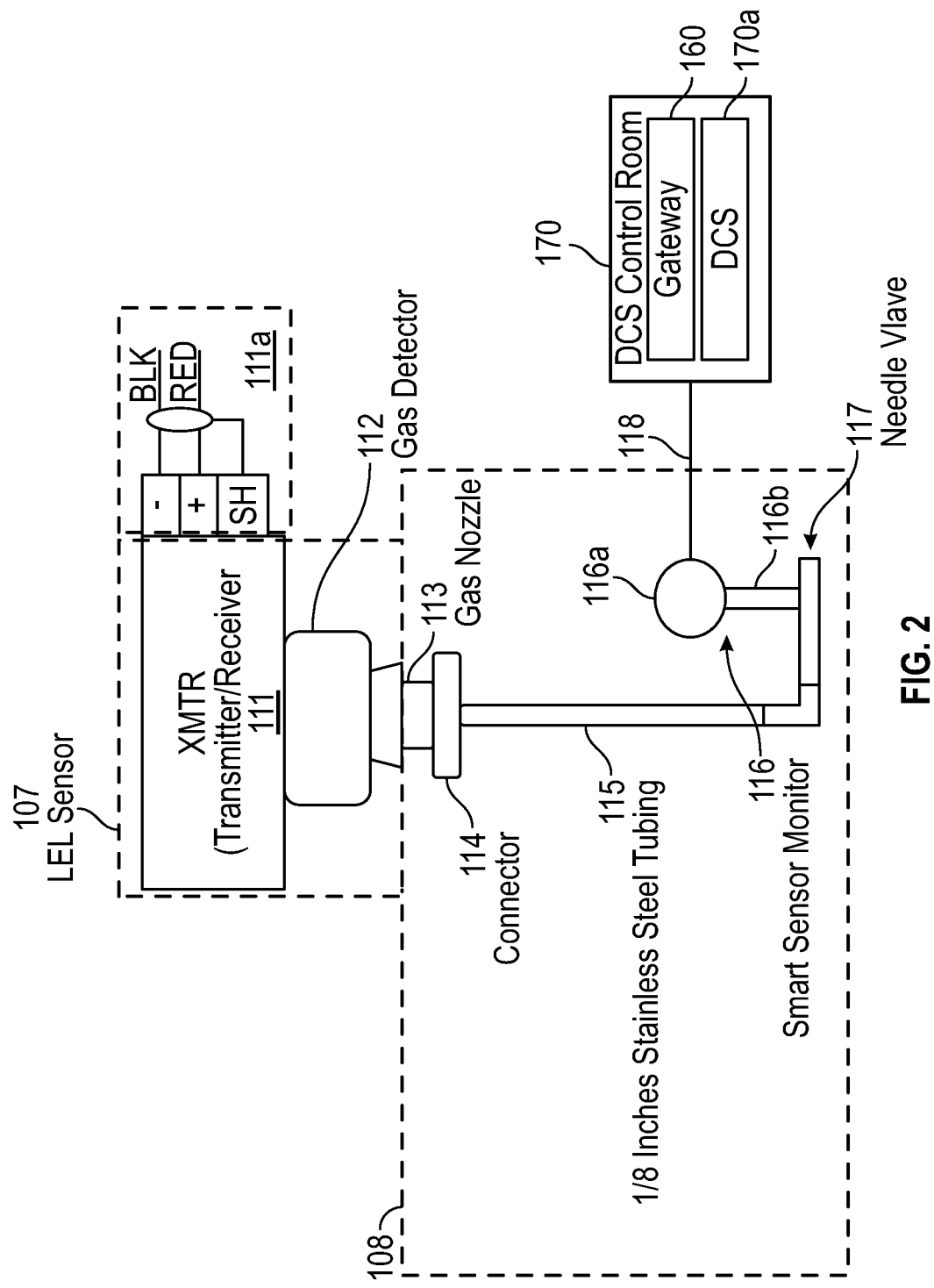

Turning to FIG. 2, FIG. 2 shows a schematic diagram in accordance with one or more embodiments. In one or more embodiments, one or more of the modules and/or elements shown in FIG. 2 may be omitted, repeated, and/or substituted. Accordingly, embodiments of the invention should not be considered limited to the specific arrangements of modules and/or elements shown in FIG. 2.

As shown in FIG. 2, FIG. 2 illustrates details of the LEL sensor (107) and the RGC assembly (108). In one or more embodiments, the LEL sensor (107) is a traditional LEL sensor that is retrofitted or otherwise modified to add the RGC assembly (108) to improve or otherwise facilitate the calibration process. The LEL sensor (107) includes a transmitter (111) and a gas detector (112). The gas detector (112) is configured to detect combustible gas in the ambient environment inside gas turbine equipment where the LEL sensor (107) is installed. During normal operation of the gas turbine, no combustible gas above the LEL concentration is detected by the gas detector (112). During a gas leak condition, leaked combustible gas above the LEL concentration is detected by the gas detector (112) that triggers the transmitter (111) to send an alarm to the DCS (170a). The alarm indicates to the DCS (170a) that a high concentration level of combustible/explosive gas is detected in the gas turbine (100). Accordingly, the DCS (170a) generates a control signal to shut down the gas turbine (100) to prevent any fire hazard.

During a calibration process, the gassing nozzle (113) allows a calibration gas (e.g., methane) to be introduced to the gas detector (112) to simulate a gas leak condition. For example, in a conventional calibration process, a technician enters or otherwise access the turbine compartment to place a canister containing calibration gas in the vicinity of the gassing nozzle (113) such that the calibration gas can be released into the gassing nozzle (113) to simulate the gas leak condition. By using LEL and RGC assemblies disclosed herein, calibration gas may be provided to the gas detector (112) without manually entering and accessing the gas turbine equipment. Additionally, embodiments described herein may refer to the gas being flowed through an RGC assembly to an LEL sensor as "calibration gas." However, one of ordinary skill in the art may appreciate that various types of gas may be flowed through an RGC assembly to an LEL sensor for purposes other than calibration, such as different types of sensor testing. Thus, "calibration gas" may be interchangeably referred to as "test gas" or merely "gas."

As shown in FIG. 2, the RGC assembly (108) includes a gassing nozzle (113), a connector (114), a tubing (115), a smart sensor monitor (116), and a needle valve (117). The tubing (115) may be made of metal or a corrosion resistant material, such as stainless steel. In some embodiments, the tubing (115) may have an ⅛" diameter and a suitable length to transport calibration or test gas from an accessible location outside of the gas turbine equipment to the LEL sensor (107). When the RGC assembly (108) is installed adjacent to the LEL sensor (107), the length of the tubing (115) allows the smart sensor monitor (116) and the needle valve (117) to be located external to the gas turbine equipment (e.g., a gas turbine compartment) where the LEL sensor (107) is installed. Locating the smart sensor monitor (116) and the needle valve (117) external to the gas turbine equipment makes the calibration of the LEL sensor (107) easier and without the extra effort to reach inside the gas turbine equipment, which would disturb operation flexibility and increase down time of the gas turbine.

The needle valve (117) may be connected to a canister of gas. The needle valve (117) is used to control the flow of the gas into the tubing (115) and to the gassing nozzle (113) via the connector (114). The LEL sensor modification to connect the retrofitted RGC assembly (108) does not affect the normal operation of the LEL sensor (107) to detect leaked combustible gas in the ambient environment where the LEL sensor (107) is installed. This is because the gassing nozzle (113) provides the connector (114) a flow path without blocking the gas detector (112) from the ambient environment.

During a calibration process, the RGC assembly (108) may be blocked from ambient air and direct a calibration or test gas from the needle valve (117) to the gas detector (112) for calibration or testing sensor accuracy. The RGC (108) is used manually with an external pressure regulator to supply calibration gas to the LEL sensor (107) through the tubing (115). The pressure regulator measures the flow of supplied calibration gas to the RGC (108). This simple assembly is a robust mechanism for sensor calibration and testing and it will not affect the integrity of the overall turbine system.

The smart sensor monitor (116) includes a calibration analyzer device (116a) and a sensor probe (116b). The smart sensor monitor (116), in particular the sensor probe (116b) is in communication with the flow path through the tubing (115), such that the sensor monitor (116) may detect one or more indicators of gas being sent through the tubing, register calibration history, register LEL sensors calibrated ranges, and register other calibration or testing data. In one or more embodiments, the sensing element in the smart sensor monitor (116) is exposed to the gas flowing from the needle valve (117) through the tubing (115) and detects each continuous passage of gas to register (i.e., detect and record) an occurrence of a calibration or testing process.

The smart sensor monitor (116), in particular the calibration analyzer device (116a), includes a computer processor and memory to log or otherwise record the occurrence and related data of a calibration or testing process that is detected and registered by the sensing element. For example, the related information may include one or more of the timestamp, duration, and concentration of the gas flow through the RGC assembly. In addition, the smart sensor monitor (116) includes internal computing feature to determine future calibration or testing due dates and generate preventive maintenance reminders according to a pre-determined preventive maintenance schedule. Further, the smart sensor monitor (116) may include a miniaturized computer system embodied in a semiconductor integrated circuit chip that is similar to the computer system (400) described below with regard to FIG. 4 and the accompanying description.

In one or more embodiments, the smart sensor monitor (116) communicates all data through wireless communication link (118) to a gateway (160) installed in a DCS control room (170). For example, the communicated data may include notifications or alarm signals for the maintenance personnel to be sent for overdue LEL sensor calibrations or testing. The gateway (160) may thus act as a communication gateway to communicate LEL sensor status with an existing DCS (170a) over Modbus TCP/IP communication. Therefore, LEL sensors status may be monitored through the existing DCS (170a).

Retrofitting an LEL sensor (107) with an RGC assembly (108) can be achieved through simple assembly (and optionally using accessory parts (e.g., nuts, screws, etc.)) to connect the tubing (115) to the gassing nozzle (113) via the connector (114) to direct gas to the gas detector (112) from a source external to the gas turbine equipment in which the LEL sensor is installed.

The components required for the LEL sensor (107), in particular the gas detector (112) to be calibrated remotely include a stainless steel type remote junction box (111a), a rectangular duct mounting kit, and the RGC assembly (108). As shown in FIG. 2, the junction box (111a) is termination between the gas sensor transmitter (111) and remote junction box (111a) to provide appropriate connections. Each inaccessible the turbine compartment may be fitted with at least one sensor (107) and RGC assembly (108). The installation of RGC assembly (108) in the duct may include making a suitable access through a gas turbine equipment containing an LEL sensor (107) and connecting the RGC assembly (108) with the LEL sensor (107). The RGC assembly (108) may be connected to the LEL sensor (107) by connecting the tubing (115) through the equipment access and connecting a first end of the tubing to the LEL sensor (107). The needle valve (117) may be connected to the opposite, second end of the tubing (positioned outside of the gas turbine equipment when installed).

Figure 3:
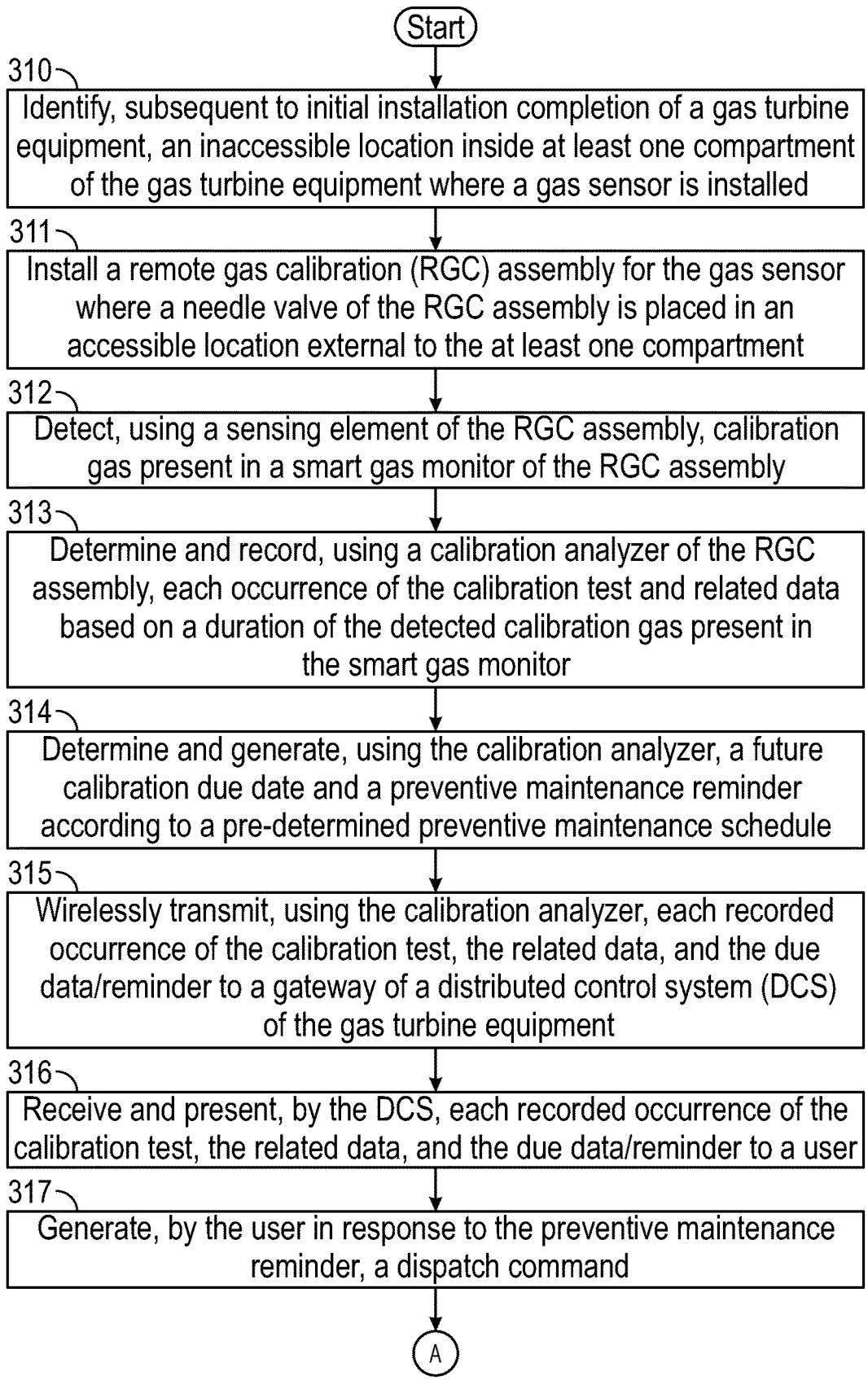
FIG. 3 shows a flowchart in accordance with one or more embodiments.
Figure 3:
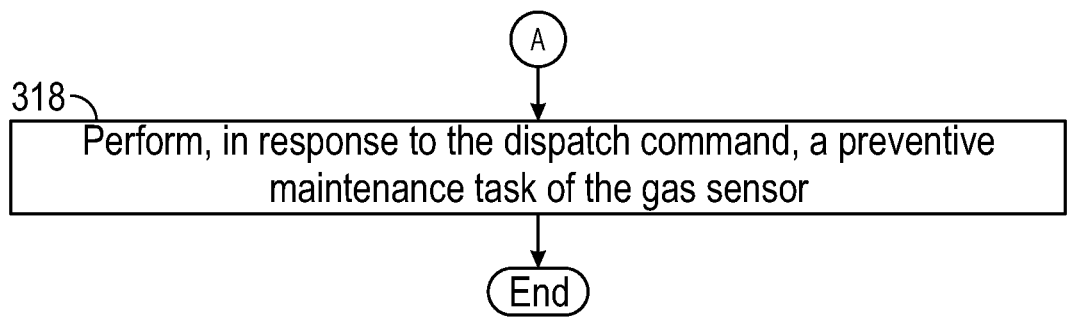

FIG. 3 shows a flowchart in accordance with one or more embodiments. Specifically, FIG. 3 describes a method of performing LEL sensor calibration in a gas turbine facility. One or more blocks in FIG. 3 may be performed using one or more components as described in FIGS. 1-2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Turning to FIG. 3, initially in Block 310, an inaccessible location is identified inside at least one compartment of a gas turbine where a gas sensor (e.g., LEL sensor 107) is installed. In one or more embodiments, one or more such inaccessible locations are identified subsequent to initial installation completion of the gas turbine equipment.

In Block 311, a remote gas calibration (RGC) assembly is installed for the gas sensor at the identified inaccessible location. The RGC assembly may be installed by extending the RGC assembly tubing through the gas turbine compartment and connecting a first end of the RGC assembly tubing to the gas sensor via a connector. In one or more embodiments, a needle valve of the RGC assembly is connected at a second end of the RGC assembly tubing and placed in an accessible location external to the gas turbine compartment where the gas sensor is installed. In one or more embodiments, the installation of the RGC assembly for the gas sensor is performed as a retrofit in response to identifying the inaccessible location.

When the RGC assembly is connected to the gas sensor in the gas turbine compartment, a gas sensor calibration may be performed by directing gas from a gas source located exterior to the gas turbine compartment, through the RGC assembly, to the gas sensor inside the gas turbine compartment. In Block 312, during each gas sensor calibration, presence of calibration gas through the RGC assembly is detected using a sensing element in a smart gas monitor of the RGC assembly.

In Block 313, each occurrence of the calibration test is registered (i.e., determined and recorded) using a calibration analyzer of the RGC assembly based on a duration of the detected calibration gas present in the smart gas monitor. Further, related data (e.g., a timestamp, duration, and concentration of the calibration gas) of each occurrence of the calibration is registered (i.e., determined and recorded) using the calibration analyzer.

In Block 314, in response to a most recent occurrence of the calibration test, a future calibration due date is determined using the calibration analyzer according to a predetermined preventive maintenance schedule. In addition, a preventive maintenance reminder is generated using the calibration analyzer by at least comparing the future calibration due date and a current date.

In Block 315, each recorded occurrence and related data of the calibration test is wirelessly transmitted using the calibration analyzer to a gateway of a distributed control system (DCS) of the gas turbine. Similarly, the future calibration due date and/or the preventive maintenance reminder are wirelessly transmitted using the calibration analyzer to the gateway of the DCS.

In Block 316, each recorded occurrence and related data of the calibration test are received and presented by the DCS to a user. Similarly, the future calibration due date and/or the preventive maintenance reminder are received and presented by the DCS to the user.

In Block 317, a dispatch command is generated by the user in response to the preventive maintenance reminder.

In Block 318, a preventive maintenance task of the gas sensor is performed in response to the dispatch command.

The method shown in FIG. 3 describes using assemblies of the present disclosure for calibration purposes of a gas sensor in a gas turbine. However, one or more steps described in FIG. 3 may be used for other types of gas sensor tests.

Figure 4:
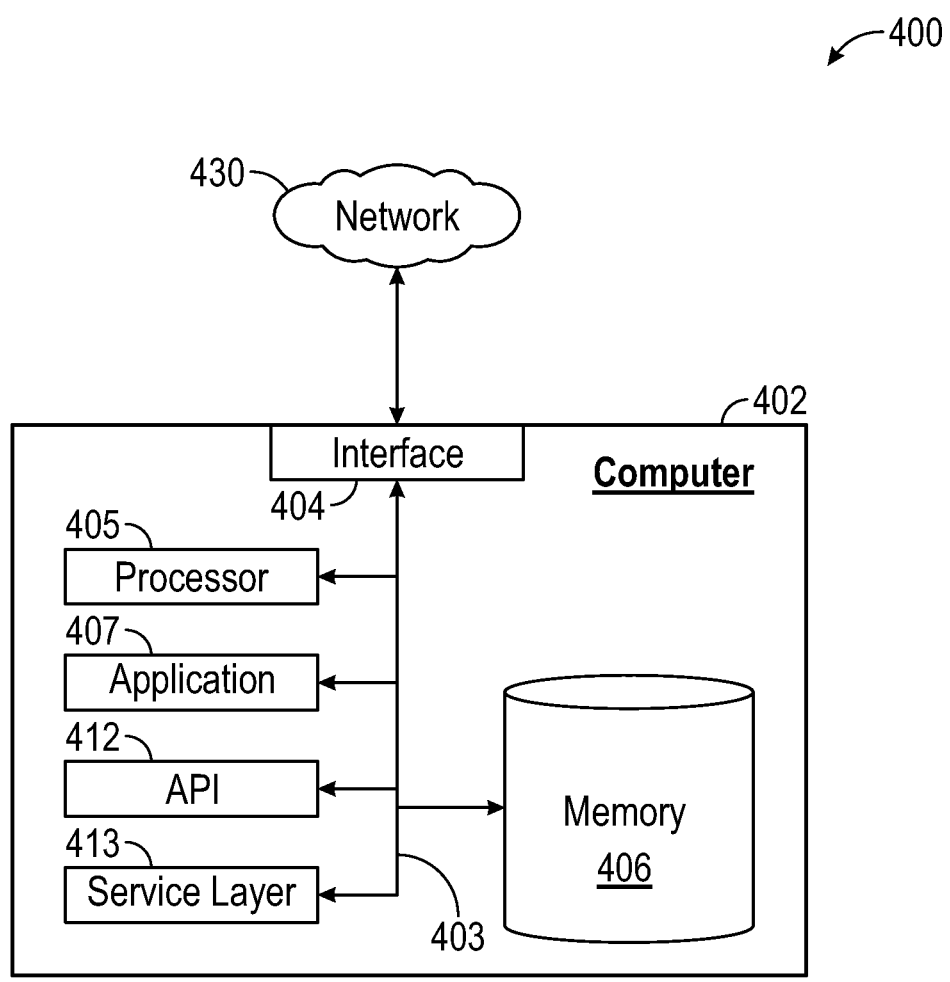
FIG. 4 shows a computing system in accordance with one or more embodiments.

Embodiments according to the present disclosure may be implemented on a computer system. FIG. 4 is a block diagram of a computer system (402) used to provide computational functionalities associated with described algorithms, methods, functions, processes, flows, and procedures as described in the instant disclosure, according to an implementation. The illustrated computer (402) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (402) may include a computer that includes an input device, such as a keypad, keyboard, touch screen, or other device that can accept user information, and an output device that conveys information associated with the operation of the computer (402), including digital data, visual, or audio information (or a combination of information), or a GUI.

The computer (402) can serve in a role as a client, network component, a server, a database or other persistency, or any other component (or a combination of roles) of a computer system for performing the subject matter described in the instant disclosure. The illustrated computer (402) is communicably coupled with a network (430). In some implementations, one or more components of the computer (402) may be configured to operate within environments, including cloud-computing-based, local, global, or other environment (or a combination of environments).

At a high level, the computer (402) is an electronic computing device operable to receive, transmit, process, store, or manage data and information associated with the described subject matter. According to some implementations, the computer (402) may also include or be communicably coupled with an application server, e-mail server, web server, caching server, streaming data server, business intelligence (BI) server, or other server (or a combination of servers).

The computer (402) can receive requests over network (430) from a client application (for example, executing on another computer (402)) and responding to the received requests by processing the said requests in an appropriate software application. In addition, requests may also be sent to the computer (402) from internal users (for example, from a command console or by other appropriate access method), external or third-parties, other automated applications, as well as any other appropriate entities, individuals, systems, or computers.

Each of the components of the computer (402) can communicate using a system bus (403). In some implementations, any or all of the components of the computer (402), both hardware or software (or a combination of hardware and software), may interface with each other or the interface (404) (or a combination of both) over the system bus (403) using an application programming interface (API) (412) or a service layer (413) (or a combination of the API (412) and service layer (413). The API (412) may include specifications for routines, data structures, and object classes. The API (412) may be either computer-language independent or dependent and refer to a complete interface, a single function, or even a set of APIs. The service layer (413) provides software services to the computer (402) or other components (whether or not illustrated) that are communicably coupled to the computer (402). The functionality of the computer (402) may be accessible for all service consumers using this service layer. Software services, such as those provided by the service layer (413), provide reusable, defined business functionalities through a defined interface. For example, the interface may be software written in JAVA, C++, or other suitable language providing data in extensible markup language (XML) format or other suitable format. While illustrated as an integrated component of the computer (402), alternative implementations may illustrate the API (412) or the service layer (413) as stand-alone components in relation to other components of the computer (402) or other components (whether or not illustrated) that are communicably coupled to the computer (402). Moreover, any or all parts of the API (412) or the service layer (413) may be implemented as child or sub-modules of another software module, enterprise application, or hardware module without departing from the scope of this disclosure.

The computer (402) includes an interface (404). Although illustrated as a single interface (404) in FIG. 4, two or more interfaces (404) may be used according to particular needs, desires, or particular implementations of the computer (402). The interface (404) is used by the computer (402) for communicating with other systems in a distributed environment that are connected to the network (430). Generally, the interface (404) includes logic encoded in software or hardware (or a combination of software and hardware) and operable to communicate with the network (430). More specifically, the interface (404) may include software supporting one or more communication protocols associated with communications such that the network (430) or interface's hardware is operable to communicate physical signals within and outside of the illustrated computer (402).

The computer (402) includes at least one computer processor (405). Although illustrated as a single computer processor (405) in FIG. 4, two or more processors may be used according to particular needs, desires, or particular implementations of the computer (402). Generally, the computer processor (405) executes instructions and manipulates data to perform the operations of the computer (402) and any algorithms, methods, functions, processes, flows, and procedures as described in the instant disclosure.

The computer (402) also includes a memory (406) that holds data for the computer (402) or other components (or a combination of both) that can be connected to the network (430). For example, memory (406) can be a database storing data consistent with this disclosure. Although illustrated as a single memory (406) in FIG. 4, two or more memories may be used according to particular needs, desires, or particular implementations of the computer (402) and the described functionality. While memory (406) is illustrated as an integral component of the computer (402), in alternative implementations, memory (406) can be external to the computer (402).

The application (407) is an algorithmic software engine providing functionality according to particular needs, desires, or particular implementations of the computer (402), particularly with respect to functionality described in this disclosure. For example, application (407) can serve as one or more components, modules, applications, etc. Further, although illustrated as a single application (407), the application (407) may be implemented as multiple applications (407) on the computer (402). In addition, although illustrated as integral to the computer (402), in alternative implementations, the application (407) can be external to the computer (402).

There may be any number of computers (402) associated with, or external to, a computer system containing computer (402), each computer (402) communicating over network (430). Further, the term "client," "user," and other appropriate terminology may be used interchangeably as appropriate without departing from the scope of this disclosure. Moreover, this disclosure contemplates that many users may use one computer (402), or that one user may use multiple computers (402).

In some embodiments, the computer (402) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Embodiments provide the following advantages for a gas turbine facility: (1) improve operation excellence process matrices key performance index (KPI), specifically for innovation, learning and continuous improvement, risk management and financial resources (energy efficiency) enabling elements, (2) adopt/customize internal innovation and technology deployment in line with best practices, (3) resolve high level organization challenges and close business needs and technology gaps, (4) provide full integration of energy efficiency and alignment of corporate policy statement for energy performance improvements, (5) enhance gas turbine PM sensors procedures and operation flexibility, (6) increases protection and safety of plant personnel and equipment, (7) improve major maintenance cost index (MCI) which will add more corporate value creation as part of company focus area of improvements, (8) improve major equipment trip index that constitutes for operational efficiency of focus area enhancements, (9) avoid turbine shutdowns and extended outages, (10) enhance business sustainability as part of main focus area of improvements, (11) ensure turbine mechanical components working at peak performance, (12) allow easy access to inaccessible remote sensors inside the turbine enclosure compartments, (13) enable technology scalability across oil and gas industry operation, (14) increase protection and safety of plant personnel and equipment, (15) decrease nuisance alarms and trips for turbine operation, (16) improve maintenance efficiency and downtime by reducing manpower hours required, (17) optimize maintenance costs for associated sensor calibration tasks, (18) reduce the associated costs for scaffolding and man-hours of preventive maintenance, (19) contribute to cooperate added value for operation facility related to gas turbine operation, reliability, equipment down time and maintenance cost savings and safety measures compliance, (20) reduce inventory rounds with benefits of timely efficiency data and more data accuracy, (21) overcome accessibility challenges in the operation work environment, (22) mitigate potential maintenance work risk such as encountering sharp edges of ducts, climbing the scaffold and entering ducts, etc. while performing the sensor calibration, (23) ensure gas turbine system integrity.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method for preventive maintenance of a gas sensor in a gas turbine, comprising:
installing a remote gas calibration (RGC) assembly to the gas turbine, comprising:
coupling a connector of the RGC assembly to the gas sensor, wherein the gas sensor detects leaked combustible gas in the gas turbine and wirelessly transmits an alert to a distributed control system (DCS) of the gas turbine,
wherein the gas sensor is installed in an inaccessible location inside a gas turbine equipment of the gas turbine, and wherein, when the RGC assembly is installed, the RGC assembly has a tubing that extends from the connector coupled to the gas sensor inside the gas turbine equipment to an accessible location external to the gas turbine equipment, and wherein a needle valve is provided at an external end of the tubing in the accessible location;

directing a calibration gas through the needle valve and the tubing to the gas sensor;

detecting, using a sensing element in a smart gas monitor separate from the gas sensor and provided in flow communication with the tubing, the calibration gas present in the tubing;

determining and recording, using a calibration analyzer in the smart gas monitor, calibration data associated with the calibration gas directed through the tubing; and wirelessly transmitting, using the calibration analyzer and separate from the gas sensor wirelessly transmitting the alert, the calibration data to a gateway of a distributed control system (DCS) of the gas turbine.

2. The method according to claim 1, wherein the data comprises a timestamp, duration, and concentration of the gas flowing through the tubing.

3. The method according to claim 1, further comprising:

determining, using the calibration analyzer and in response to the data collected in a first calibration test, a future calibration due date according to a pre-determined preventive maintenance schedule;

wirelessly transmitting, using the calibration analyzer, the future calibration due date to the gateway;

receiving and presenting, by the DCS, the future calibration due date to a user.

4. The method according to claim 3, further comprising:

generating, by at least comparing the future calibration due date and a current date, a preventive maintenance reminder;

wirelessly transmitting the preventive maintenance reminder to the gateway; and receiving and presenting, by the DCS, the preventive maintenance reminder to the user.

5. The method according to claim 4, further comprising:

generating, by the user in response to the preventive maintenance reminder, a dispatch command; and performing, in response to the dispatch command, a preventive maintenance task of the gas sensor.

6. The method according to claim 1, wherein the RGC assembly is installed as a retrofit after the gas sensor has been installed in the gas turbine.

* * * * *